United States Patent [19]
Roache

[11] 4,067,330
[45] Jan. 10, 1978

[54] BED SORE BANDAGE COVER

[75] Inventor: Mina V. Roache, Jamaica, N.Y.

[73] Assignee: The Raymond Lee Organization, Inc., New York,, N.Y.

[21] Appl. No.: 696,291

[22] Filed: June 15, 1976

[51] Int. Cl.² .......................................... A61B 19/00
[52] U.S. Cl. .................................................. 128/149
[58] Field of Search ................... 128/132 R, 149, 157; 5/338

[56] References Cited
U.S. PATENT DOCUMENTS

| 2,056,767 | 10/1936 | Blath | 128/149 |
| 3,020,910 | 2/1962 | Ward | 128/149 |
| 3,216,417 | 11/1965 | Posey | 128/149 |

FOREIGN PATENT DOCUMENTS

| 430,638 | 6/1926 | Germany | 128/149 |
| 261,010 | 8/1927 | United Kingdom | 128/149 |

Primary Examiner—Lawrence W. Trapp
Attorney, Agent, or Firm—Stephen Wyden

[57] ABSTRACT

A pad forming a concave lower edge and a concave upper edge and forming a plurality of air openings through the surface of the pad is attached around a buttocks area of a user by a strap with a button hole connecting to a strap with a button at a distal end of the strap, additional straps attached to the lower concave edge of the pad pass through the groin of the user and engage additional button holes formed in the straps that go around the body of the user, the pad may be filled with a sponge rubber material, and a bandage may be secured by the pad to the buttocks area of the user to cover bed sores.

5 Claims, 4 Drawing Figures

BED SORE BANDAGE COVER

I have invented a new and novel bed sore pad. This pad may be attached around the portion of a patient in the hospital that has developed bed sores and will cushion the affected area while providing for air circulation around the affected area. Furthermore, this pad is so constructed that the user may carry out eliminatory and excretory functions while wearing the pad.

My invention can be understood in view of the accompanying figures.

Figure 1:
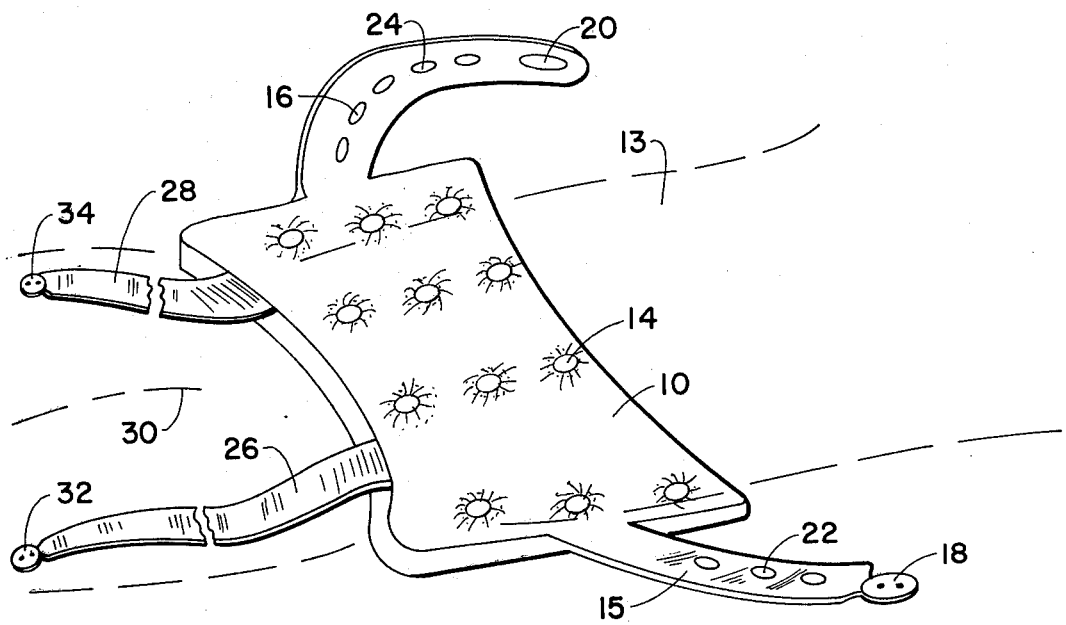
FIG. 1 shows the pad about to be attached around a user's body.
Figure 2:
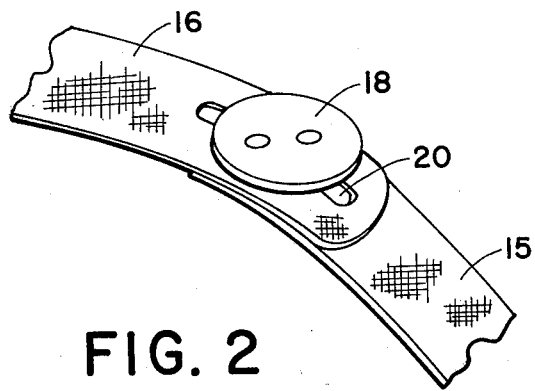
FIG. 2 is a close up of the connection between the straps.
Figure 3:
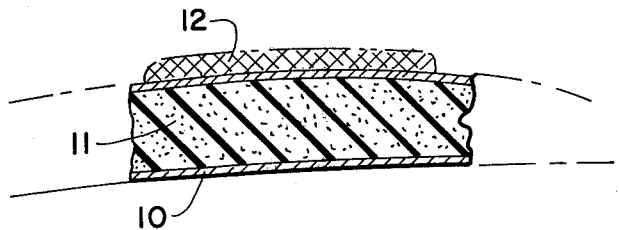
FIG. 3 is a cross section of a section of the pad with a bandage mounted on a surface of the pad.
Figure 4:
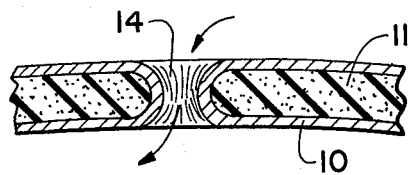
FIG. 4 is a cross section of a section of the pad through one of the air openings.

With regard to FIGS. 1, 2, 3, and 4, a pad 10 containing a sponge rubber material 11 may have a bandage 12 attached to a surface of the pad 10. The bandage may then be applied to the skin of the user 13 with the air openings 14 formed through the pad providing circulation to the skin of the user 13 and to the bandage 12. Elastic straps 15 and 16 can be connected together around the body of the user 13 by a button 18 attached to a distal end of strap 15 engaging with button hole 20 of elastic strap 16. A plurality of additional button holes 22 in elastic strap 15 and 24 in elastic strap 16 are provided to engage the bottom straps 26 and 28 which may pass through the groin area between the legs 30 of the user 13. Buttons 32 and 34 attached to the distal ends of straps 26 and 28 engage the button hols 22 and 24 securing the pad 10 with its concave lower and upper edges around the buttocks area of the user 13.

Having described a preferred embodiment of my invention, it is understood that various changes can be made without departing from the spirit of my invention, and, I desire to cover by the appended claims all such modifications as fall within the true spirit and scope of my invention.

What I claim and seek to secure by Letters Patent is:

1. A pad for use over bed sores, comprising:
    a pad forming a concave lower edge and forming a concave upper edge,
    a small round air opening formed through the pad, and means of attaching the pad around a buttocks area of a user.

2. The pad of claim 1, wherein the pad is filled with a sponge rubber material.

3. The pad of claim 2, wherein the means of attachment comprises:
    an elastic strap attached to a side of the pad,
    a second elastic strap attached to another side of the pad,
    a button attached to a distal end of the strap,
    the second strap forming a button hole at a distal end of the second strap and engaging the button when the straps are passed around a portion of a user's body,
    a strap attached to the lower concave edge of the pad,
    a button attached to a distal end of the strap attached to the lower concave edge of the pad, and
    one of the straps attached to the sides of the pad forming an additional button hole to engage the button attached to the strap attached to the concave lower edge of the pad.

4. The pad of claim 3, further comprising:
    the strap made of an elastic material, and the second strap made of an elastic material.

5. The pad of claim 4, wherein a bandage is mountable between the pad and a buttock of a user.

* * * * *